United States Patent [19]

Gero

[11] Patent Number: 5,223,395
[45] Date of Patent: Jun. 29, 1993

[54] IMMUNOMETRIC ASSAYS FOR TUMOR NECROSIS FACTOR-ALPHA AND METHODS FOR PREVENTING THE LOSS OF BIOLOGICAL ACTIVITY OF TUMOR NECROSIS FACTOR-ALPHA IN BIOLOGICAL SAMPLES

[75] Inventor: Eva J. Gero, West Chester, Pa.

[73] Assignee: Centocor, Inc., Malvern, Pa.

[21] Appl. No.: 278,605

[22] Filed: Dec. 1, 1988

[51] Int. Cl.$^5$ .................. G01N 33/53; C07K 15/28; C07K 13/00; C12N 5/12

[52] U.S. Cl. .................................. 435/71; 435/7.94; 435/240.27; 530/351; 530/388.23; 436/548

[58] Field of Search ........... 435/7, 810, 172.2, 240.27, 435/7.1, 7.94; 436/501, 504, 518, 528, 531, 534, 536, 538, 540, 547, 548, 164, 172, 176, 800, 804, 805, 815, 826; 530/351, 387, 388.24, 888.23, 240.27

[56] References Cited

U.S. PATENT DOCUMENTS

| | | | |
|---|---|---|---|
| 4,447,355 | 5/1984 | Sakamoto et al. | 424/85.2 |
| 4,457,916 | 7/1984 | Hayashi et al. | 424/85.2 |
| 4,743,541 | 10/1988 | Higgins et al. | 435/7.92 |

FOREIGN PATENT DOCUMENTS

| | | |
|---|---|---|
| 0288088 | 10/1988 | European Pat. Off. |
| WO86/03498 | 6/1986 | PCT Int'l Appl. |
| WO88/09508 | 12/1988 | PCT Int'l Appl. |

OTHER PUBLICATIONS

Wong et al., *Science*, vol. 242, pp. 941-944 (Nov. 11, 1988).
Fomsgaard et al., *Scand. J. Immunol.*, vol. 27, pp. 143-147 (1988).
Bringman et al., *Hybridoma*, vol. 6 (5), pp. 489-507 (1987).
Gibco Laboratories, Grand Island, N.Y., p. 44. 1987.
Prince et al. *J. Pharmaceutical & Biomedical Analysis*, vol. 5, No. 8 pp. 793-802, Dec. 12, 1987.
Simpson et al. *Critical Care Clinics* vol. 5 1989.
Tietz, N. W. *Fundamentals of Clinical Chemistry*, 1976, W. B. Saunders Co.
Stansfield, W. D. *Serology* and *Immunology* A Clinical Approach, Macmillan Publ., 1981.
C. M. Liang et al., *Biochem. Biophys. Res. Comm.*, 137: 847-854 (1986).
J. M. Davis et al., *Biochemistry* 26: 1322-1326 (1987).
R. A. Smith and C. Baglioni, *J. Biol. Chem.*, 262: 6951-6954 (1987).
N. Sunahara et al., *Chemical Abstracts*, vol. 109, No. 7, p. 469, Abstract No. 4887m 1988.

*Primary Examiner*—David L. Lacey
*Assistant Examiner*—Paula Hutzell
*Attorney, Agent, or Firm*—Hamilton, Brook, Smith & Reynolds

[57] ABSTRACT

An immunometric assay is disclosed for biologically active tumor necrosis factor in a biological sample comprising, forming a complex of a first labeled monoclonal antibody, biologically active TNF, and a second monoclonal antibody which can be bound to an insoluble substrate and detecting the amount of label associated with the complex. The assay is characterized by employing first and second monoclonal antibodies which react with the same epitopic site on TNF-alpha monomer. A method is also disclosed for blocking accelerated TNF degradation in a non-preserved biological sample, such as blood, comprising contacting the biological sample with EDTA, luminol, or a combination thereof.

8 Claims, 2 Drawing Sheets

IMMUNOMETRIC ASSAYS FOR TUMOR NECROSIS FACTOR-ALPHA AND METHODS FOR PREVENTING THE LOSS OF BIOLOGICAL ACTIVITY OF TUMOR NECROSIS FACTOR-ALPHA IN BIOLOGICAL SAMPLES

BACKGROUND OF THE INVENTION

Tumor necrosis factor-alpha (TNF-alpha) is a protein that is an essential mediator of the inflammatory response. TNF-alpha is identical to the hormone cachectin, which is a key endogenous factor in the pathogenesis of chronic wasting associated with acute inflammatory or malignant diseases. B. Beutler and A. Cerami, "Tumor Necrosis, Cachexia, Shock, and Inflammation: A Common Mediator", *Ann. Rev. Biochem.*, 57:505-518 (1988).

TNF-alpha has antitumor activity, causing hemorrhagic necrosis in tumors in mice treated with bacillus Calmette-Guerin (BCG) and endotoxin. TNF-alpha is the major mediator of endotoxin shock (*Science* 229:869 (1985)) in which hypotension, derangement of lipid and glucose metabolism, acidosis, and widespread neutrophil activation can lead to increased catabolic metabolism and possible death of the organism. *Ann. Rev. Biochem.* 57:505 (1988).

Cachexia, i.e., anorexia and wasting in chronic infectious or malignant diseases, is also evoked by TNF-alpha primarily through suppression of the enzyme lipoprotein lipase and by mobilization of triglycerides in adipocytes. *Mol. Biochem. Parasitol.*, 2:31 (1980). Through its complex effect on endothelial and neutrophil cells, TNF-alpha also evokes neutrophil adhesion to lung capillaries and enhances thrombus formation. This may result in disseminated intravascular coagulation, migratory thrombosis and hemorrhagic necrosis. TNF-alpha is a potent endogenous pyrogen affecting hypothalmic neurons and promoting interleukin-1 (IL-1) production. TNF has also been implicated in the pathogenesis of malaria and gram-negative septic shock. See *Ann. Rev. Biochem.* 57:505-518 (1988) supra and references cited therein.

TNF-alpha monomer is a polypeptide of 17 kd molecular weight consisting of 150-160 amino acids. B. Beutler and A. Cerami, *Nature* 320:584-588 (1986). The protein can be isolated from the supernatant of stimulated human macrophages, or, in a highly pure form, as a recombinant protein. Shirai, T. et al., *Nature*, 313:803-806 (1985). The bioactivity of TNF-alpha is indistinguishable from that of the cytotoxic polypeptide hormone lymphotoxin, produced by activated lymphocytes (also identified as TNF-beta). *Hybridoma* 6(5):489 (1987). The two molecules are structurally related, being encoded by closely linked genes within the major histocompatibility complex. *Nucleic Acid Res.* 13:6361 (1985); PNAS 83:8699 (1986). As a result, the two proteins share common receptors on a large variety of cells. TNF-alpha and beta can be distinguished from each other based on their antigenic properties but not on the basis of cytotoxic activity.

TNF-alpha is produced by all types of macrophages in a degree dependent on the maturation and differentiation state (*J. Immunology* 138:957 (1987)), as well as by T lymphocytes (*J. Exp. Med.* 165:1581 (1987)) in response to a variety of invasive stimuli. The most potent known stimulus is the bacterial lipopolysaccharide (LPS). Viruses, trypanosoma, plasmodium, some Gram-positive bacteria, and the lymphokine IL-1 also stimulate TNF-alpha production. Beutler and Carami, supra.

TNF-alpha is, however, subject to rapid physiochemical changes in vitro and this is likely to result in lower measured TNF values in immunoassays as compared in in vivo concentrations. TNF-alpha dissociates and aggregates to yield a protein of variable size. The biologically active form of TNF-alpha is believed to be a dimeric or trimeric species. Smith, R. A. and C. Baglioni, *J. Biol. Chem.* 262:6951-6954 (1987); Davis, J. M. et al., *Biochemistry*, 26:1322-1326. Dissociation of the trimeric protein is believed to be responsible for the instability of biologically active TNF-alpha in dilute solutions. Smith and Baglioni, Id. A failure to detect TNF-alpha activity in stored sera has also been reported. *Blood* 68:337 (1986); Blood 64:229 (1984).

Immunoassays for TNF-alpha have been described in the literature. For example, EPO Published Application 218,868 discloses the preparation of pure human tumor necrosis factor. The application further discloses hybridomas which produce monoclonal antibodies to human tumor necrosis factor and use of the monoclonal antibodies for diagnostic purposes. JP Published Application 60208924 discloses a monoclonal antibody to human tumor necrosis factor and its use in immunoassays.

Because the degradation of TNF-alpha in fresh, blood-derived materials such as sera or plasma can occur immediately after the biological sample is removed from the body, there has been some interest in developing a method to preserve TNF activity. Two recent U.S. Pat. Nos. 4,447,355 and 4,457,916, are directed to methods of stabilizing the activity of frozen or lyopholized TNF using albumin or a carbohydrate material. Unfortunately, neither of these methods addresses the question of preserving biologically active TNF-alpha preparations for in vitro use.

Present methods that measure TNF-alpha concentrations in biological samples (e.g., immunometric or bioassays) give result that merely reflect TNF-alpha activity after degradation, and do not accurately measure activity relevant to the situation in vivo. A method capable of preventing the accelerated degradation of TNF-alpha in fresh samples will provide a valuable tool for more accurate TNF-alpha measurements. Such a method will be useful in diagnosis and management of a variety of pathological states, infectious diseases such as gram-negative septic shock or malignant diseases.

SUMMARY OF THE INVENTION

The present invention provides an immunometric assay for human TNF-alpha in a liquid sample. The assay comprises forming a complex of (1) a first monoclonal antibody that is labeled, and which is specific for an epitope of TNF-alpha; (2) biologically active TNF-alpha, which is di- or trimeric; (3) and a second monoclonal antibody and detecting the amount of label associated with the complex as indicative of the presence or the amount of TNF-alpha in the liquid sample. The first and second monoclonal antibodies are specific for the same epitope of TNF-alpha. Biologically active TNF-apha exists as a dimer or trimer, therefore, the active form has at least two of the same epitope, which allows the complex to be formed. The preferred assay is a solid phase assay where at least one of the antibody constituents of the complex is bound to a solid phase, either before or after formation of the complex. The invention further provides a method for blocking the accelerated degradation of TNF-alpha in a biological sample comprising contacting the biological sample with an antioxidant in an amount sufficient to prevent such degradation.

DETAILED DESCRIPTION OF THE INVENTION

Figure 1:
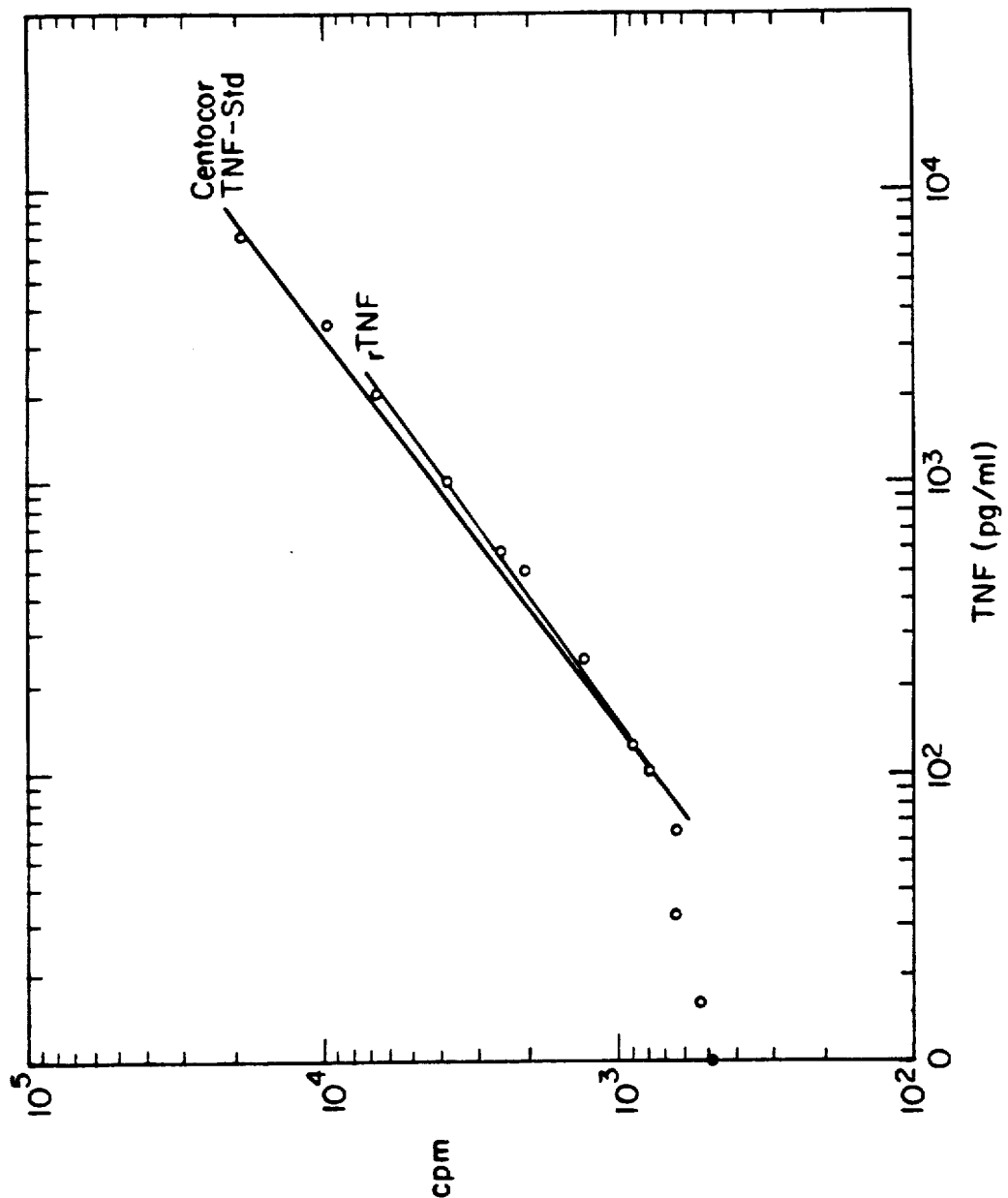
FIG. 1 shows a graph relating known TNF-alpha levels to those obtained in the monoclonal antibody 104-based immunoassay.

The present invention provides a novel immunometric assay for TNF-alpha. In another aspect, the present invention provides a novel method for blocking degradation of TNF-alpha in a biological sample.

In the immunoassay of the invention, a complex is formed comprising a labeled monoclonal antibody, biologically active TNF-alpha, and a second monoclonal antibody. The amount of complex is directly proportional to the concentration of TNF-alpha in the sample. The first and second monoclonal antibodies react with an unrepeated, epitope on the TNF-alpha monomer. Preferably the first and second monoclonal antibodies are derived from the same hybridoma cell line and react with the same epitope on the TNF-alpha monomer. The immunoassay can be conducted in a reverse, simultaneous, or forward format. Following formation of the complex, the amount of biologically active TNF is quantified by detecting the amount of label associated with the complex. Preferred assays are those where the complex is immobilized on the solid phase.

Antibodies useful in the invention are obtained by well-known hybridoma methods. An animal is immunized with TNF-alpha. A fused cell hybrid is then formed between antibody producing cells from the immunized animal and an immortalizing cell such as myeloma.

In preferred embodiments, anti-human TNF-alpha monoclonal antibodies of this invention are produced by murine hybridomas formed by fusion of: a) a mouse myeloma or hybridoma which does not secrete antibody with b) murine spleen cells which secrete antibodies obtained from mice immunized against human TNF-alpha.

Typically, the mice are immunized with a primary injection of human TNF-alpha followed by a number of boosting injections of TNF-alpha. During or after the immunization procedure, sera of the mice may be screened to identify those mice in which a substantial immune response to the TNF-alpha has been evoked. From selected mice, the spleen cells are obtained and fusions are performed. Suitable fusion techniques are the Sendai virus technique. Kohler, G. and Milstein, C., *Nature* 256:495 (1975), or the polyethylene glycol method, Kennet, R. H. in "Monoclonal Antibodies, Hybridomas—A New Dimension in Biological Analyses", ed. R. H. Kennet, T. J. McKearn and K. B. Bechtol, Plenum Press, N.Y., 1980. Also, electrofusing techniques may be employed. Zimmerman, U. and Vienken, J., *J. Membrane Bio.* 67:165 (1982).

The hybridomas are then screened for production of anti-human TNF-alpha antibody. A suitable screening technique is a solid phase radioimmunoassay. A solid phase immunoadsorbent is prepared by coupling human TNF-alpha to an insoluble matrix. The immunoadsorbent is brought into contact with culture supernatants of hybridomas. After a period of incubation, the solid phase is separated from the supernatants, then contacted with a labeled antibody against murine immunoglobulin. Label associated with the immunoadsorbent indicates the presence of hybridoma products reactive with TNF-alpha. The hybridoma products are then examined for their ability to react with natural and recombinant TNF-alpha.

The monoclonal anti-TNF-alpha antibodies can be produced in large quantities by injecting anti-human-TNF-alpha producing hybridoma cells into the peritoneal cavity of mice and, after an appropriate time, harvesting ascites fluid from the mice which yields a high titer of homogenous antibody. The monoclonal antibodies are isolated therefrom. Alternatively, the antibodies can be produced by culturing anti-human-TNF-alpha producing cells in vitro and isolating secreted monoclonal anti-human-TNF-alpha antibodies from the cell culture medium directly.

A particularly preferred antibody for use in this invention is the monoclonal antibody 104 (Mab 104), an IgG monoclonal antibody against recombinant human TNF. Preparation and characteristics of 104 are described in Liang, C. -M. et al., *Biochem. Biophys. Res. Comm.*, 137:847–854 (1986) incorporated by reference herein. Monoclonal 104 is the antibody BG4 as identified in Liang et al. (supra, Table 1, page 850). Assays of this invention utilizing 104 exhibit dose-related binding to purified natural and recombinant human TNF-alpha. Antibody 104 reacts with a specific, non-repeated epitope on the TNF-alpha monomer. Immunometric assays in which this antibody is used shows that the assay detects TNF-alpha; evidence of this derives from several sources. In a solid phase radioimmunoassay, activity of antibody binding to TNF-alpha correlates well with TNF-activity based on cytotoxicity bioassays (FIG. 1). Moreover, addition of bacterial lipopolysaccharide (LPS), a stimulator of TNF, during immunoassay procedures enhances TNF production in a dose-dependent manner.

The immunometric methods of this invention can discriminate between the active and inactive forms of human TNF-alpha. Because biologically active TNF-alpha is present as a dimeric or trimeric molecule, the preferred type of immunochemical assay for measuring biologically active TNF-alpha is a sandwich immunometric assay in which antigen (i.e.—human natural or recombinant TNF-alpha) is measured by reacting it with anti-TNF-alpha antibodies, both of which are specific for the same epitope on TNF-alpha.

In sandwich assays of this invention, a complex is formed comprising: 1) a first antibody specific for a non-repeated epitope of TNF-alpha, 2) TNF-alpha, and 3) a second antibody specific for the same epitope of TNF-alpha. This second antibody is labeled. The term "label" refers to the fact that the antibody contains a chemical group to which a label can be attached before, or after, formation of the complex. For example, the antibody can be complexed with biotin, to which a label can be attached using avidin.

The complex can be formed before it is immobilized onto a solid phase. In other embodiments, the complex can be formed on the solid phase by immobilizing the first antibody and then combining TNF-alpha to be detected and labeled antibody by introducing them simultaneously or sequentially. Sandwich assays for TNF-alpha, which in its biologically inactive configuration can be a monomer are designed by forming a complex comprising 1) a first antibody specific for an epitope on the TNF-alpha monomer; 2) TNF-alpha; and 3) a second, labeled antibody specific for a different epitope on the TNF-alpha monomer.

Figure 2:
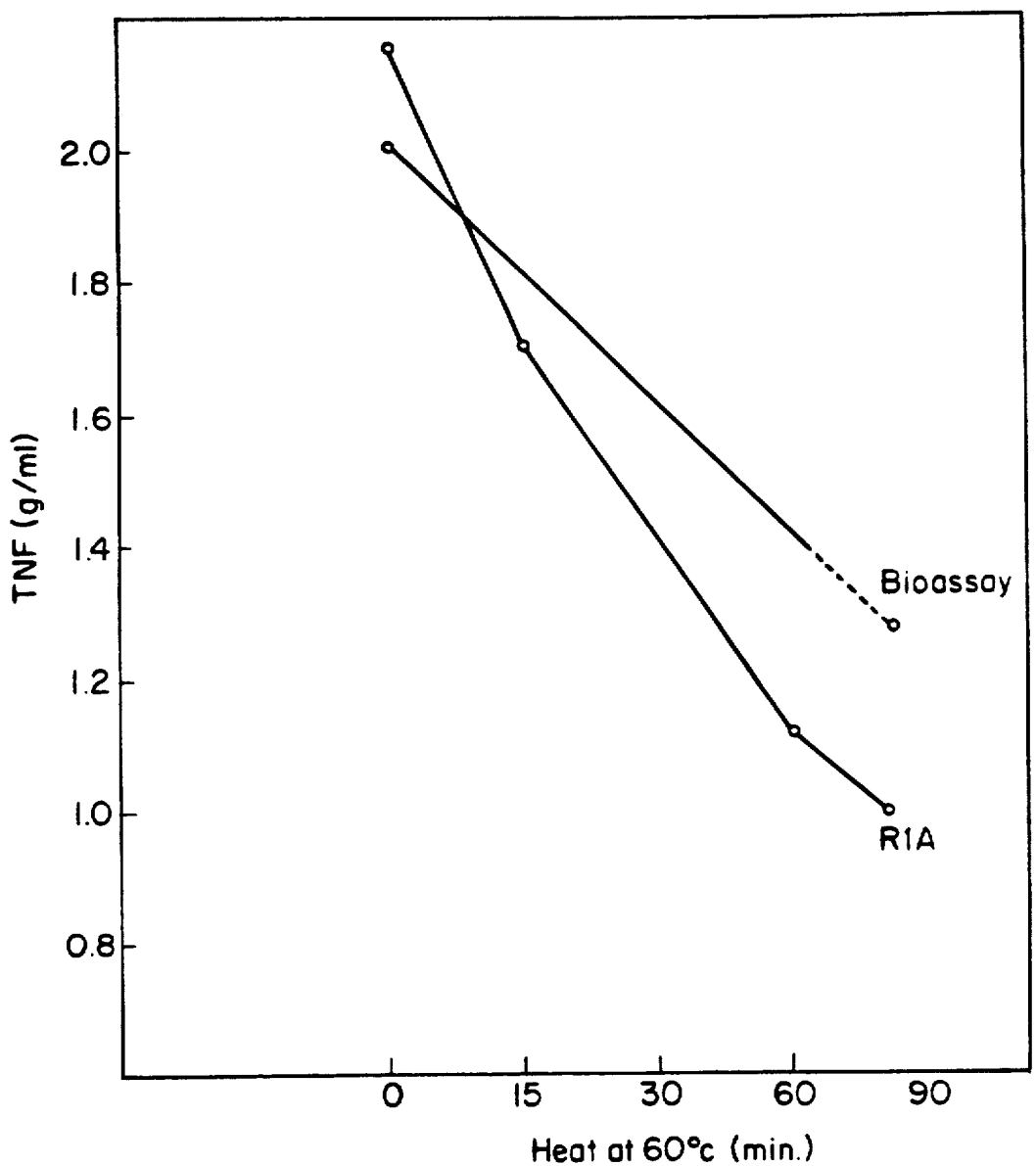
FIG. 2 shows a graph relating TNF-alpha values in a sample undergoing progressive denaturation as determined by a bioassay and a monoclonal antibody 104-based immunoassay of the invention.

In preferred embodiments, which measure biologically active TNF-alpha, the TNF-alpha is immobilized in proportional amounts on an immunoadsorbent to which is affixed an antibody specific for an epitope of TNF-alpha. This antibody specifically binds the TNF-alpha. TNF-alpha is detected by forming a complex with radiolabeled antibody directed to the same epitope of TNF-alpha. In this manner, biologically active TNF-alpha is measured (see FIG. 2).

Sandwich assays may be performed in forward, reverse or simultaneous mode. In a forward sandwich assay for human TNF-alpha, a monoclonal antibody directed against an epitope of human TNF-alpha is affixed to a solid phase. A liquid sample, such as a blood-derived fluid, containing human TNF-alpha is incubated with the immunoadsorbent. Incubation is maintained for a sufficient period of time to allow the human TNF-alpha in the liquid sample to bind the immobilized antibody on the solid phase in amounts proportional to the TNF-alpha concentration in the sample. After this first incubation, the solid phase immunoadsorbent is separated from the sample. The immunoadsorbent is washed to remove unbound human TNF-alpha and interfering substances, such as nonspecific proteins, which are also present in the liquid sample. The immunoadsorbent containing human TNF-alpha bound to immobilized antibody is subsequently incubated with labeled antibody, or antibody bound to a coupling agent such as biotin or avidin, the antibody specific for an epitope on human TNF-alpha. Labels for antibodies are well known in the art and include radionuclides, enzymes, fluors, biotin, etc. In preferred methods of this invention, this antibody is an antibody specific for the same epitope of human TNF-alpha as the immobilized antibody. The incubation is carried out for a period of time and under conditions sufficient to ensure binding of the labeled antibody to TNF-alpha in quantities proportional to the amount of TNF-alpha on the solid phase. After the second incubation, another wash is performed to remove unbound label. The label bound to the solid phase immunoadsorbent is then measured, and the amount of label detected serves as a direct measure of the amount of biologically active human TNF-alpha present in the liquid sample.

The sandwich immunoassays may also be performed in reverse and simultaneous modes. In a reverse mode immunoassay to measure biologically active TNF-alpha, an incubation mixture is formed of the liquid sample to be tested and a soluble labeled antibody, or antibody complexed with a coupling agent (i.e., biotin), the antibody directed against an epitope of human TNF-alpha (e.g., labeled 104 antibody). The mixture is incubated, then contacted with a solid phase immunoadsorbent containing a monoclonal antibody (e.g., the 104 antibody) directed against the same epitope of human TNF-alpha. After another incubation, the immunoadsorbent is separated from the mixture and the label bound to the immunoadsorbent is taken as an indication of the amount of biologically active human TNF-alpha in the liquid sample.

In the simultaneous mode, an incubation mixture is formed of the liquid sample, anti-human-TNF-alpha antibody that is labeled or antibody complexed with a coupling agent, and the solid phase immunoadsorbent. After appropriate incubation, the solid phase immunoadsorbent is separated from the mixture and the label associated with the immunoadsorbent is measured to give an indication of the amount of human TNF-alpha in the liquid sample.

For each incubation step in the various assay formats, the time, incubation conditions and reagent concentrations are selected to ensure optimal binding of human TNF-alpha to the immobilized antibody and to labeled antibody. In the preferred forward sandwich immunoassay, where two incubation steps are required, the solid phase immunoadsorbent containing immobilized antibody is incubated with the liquid sample for about 2 to about 18 hours at between room temperature and about 37° C. to obtain optimal binding. Subsequent incubation steps are performed for 2 to 6 hours in citrate buffer (pH 5.5), the buffer comprising 20% calf serum (v/v), 0.1% sodium azide (v/v), 50 ug/ml monoclonal antibody B2TT as a blocking agent, 50 mM EDTA and 10 mg/ml sodium chloride. The parameters which yield optimal binding of human TNF-alpha may be established for other formats of the immunoassay by no more than routine experimentation.

The immunoassays of this invention are used to detect and quantify human TNF-alpha in a liquid sample. Liquid samples include essentially all biological fluids such as blood, or blood-derived fluids such as plasma or serum and urine, lymph, etc. Also, the liquid sample may be a sample of a liquid medium in which monocytes or other mammalian cells have been cultured. They may also be extracts or supernatants of microbial cultures expressing recombinant human TNF.

As noted, the assays can be used to detect recombinant human TNF-alpha produced by genetically altered cells. Recombinant human TNF-alpha detectible by the assays includes human TNF-alpha expressed by genetically engineered microorganisms such as *E. coli* or genetically engineered yeast or mammalian cells.

In the solid phase immunometric assays of this invention, the monoclonal antibody reactive with human TNF-alpha is immobilized by affixing it to a solid phase to create an immunoadsorbent. In reverse or forward mode, antibody can be affixed to the solid phase before the three-part complex (i.e., labeled antibody: TNF-alpha:unlabeled antibody) is formed. This tripartite or ternary complex can also be attached to a solid phase after the complex is formed. This can be accomplished, for example, by affixing avidin to the solid phase and allowing the ternary complex to form in solution, one antibody of this complex being labeled with biotin.

Many types of solid-phases may be employed. Well-known solid phases include beads formed from glass, polystyrene, polypropylene, dextran, and other materials; tubes formed from or coated with such materials, etc. The antibody can be either covalently or noncovalently bound to the solid-phase by techniques such as covalent bonding via an amide or ester linkage or adsorption. Those skilled in the art will know many other suitable solid-phases and methods for immobilizing antibodies thereon, or will be able to ascertain such using no more than routine experimentation.

In the various solid phase assays of this invention, the immunoadsorbent is separated from incubation mixtures containing the liquid sample, the labeled antibody or both. The immunoadsorbent is washed prior to contacting it, when required, with a second incubation medium and prior to measuring the amount of label associated with the immunoadsorbent. The washing removes non-specific interfering substances or excess labeled antibody which may affect the accuracy and sensitivity of the assay.

In each of the immunoassays of this invention, monoclonal anti-human TNF-alpha antibody directed against an epitope of human TNF-alpha is also used as the labeled antibody (tracer). Such antibodies can be labeled directly with a radioactive material, such as $^{125}I$; labeled with an optical label, such as fluorescent material; labeled with an enzyme; or labeled by some other technique. The antibodies can also be labeled indirectly, by complexation with another labeled antibody.

To determine the amount of human TNF-alpha in the liquid sample, either the amount of label associated with the immunoadsorbent or the amount of unbound label, that is, labeled antibody which remains in soluble form, is measured. Generally, it is preferable to measure the label bound to the immunoadsorbent. The label may be detected by a gamma counter, for example, if the label is a radioactive gamma emitter, or by a fluorimeter, if the label is a fluorescent material. In the case of an enzyme label, detection may be accomplished by colorimetric methods employing a material capable of acting as a substrate for the enzyme.

The measured amount of label detected is then compared to a quantitative relationship between the amount of label and the amount of biologically active human TNF-alpha. The quantitative relationship can be determined by performing the assay with standards (i.e. samples containing known amounts of biologically active human TNF-alpha). For several such samples containing different amounts of human TNF-alpha, the assay is conducted and the amount of label either bound or unbound to the immunoadsorbent is determined; a curve is constructed defining the quantitative relationship between the amount of label and the amount of human TNF-alpha. By reference to the curve, the amount of human TNF-alpha in a liquid sample containing an unknown amount of human TNF-alpha can be determined from the amount of label detected.

The immunoassays described provide rapid, highly sensitive, inexpensive and reproducible methods for detection and quantification of natural or recombinant human TNF-alpha. The assays provide a substitute for existing bioassays for TNF-alpha which are semi-quantitative, much more time-consuming, variable, much less specific and cannot be performed routinely in hospital laboratories. The stability of the samples employed in the assays of this invention is significantly improved by the method described for preventing degradation of TNF in blood. Thus, the assay may be provided conveniently in kits for clinical or research purposes.

The assays may be employed by hospitals or clinical laboratories to determine levels of human TNF-alpha in serum, plasma or other biological fluids of patients. The assay may also be used to monitor the ability of a patient to produce TNF-alpha during the course of infectious diseases. This will be of predictive value in managing the course of treatment in a variety of disease states. In addition, the assays may be used to monitor the production of biologically active TNF-alpha by cultured mammalian cells or by genetically engineered microorganisms.

The reagents for performing the assays of this invention may be assembled in assay kits. For instance, a kit for performing an immunoassay for biologically active human TNF-alpha in blood would comprise a solid phase immunoadsorbent containing an antibody specific for a non-repeated epitope of human TNF-alpha (e.g. Mab 104), a labeled antibody specific for the same epitope of TNF-alpha (e.g. Mab 104) and, optionally, human TNF-alpha standards.

The labile nature of TNF-alpha results in its conversion to a biologically-inactive form. It is believed that contact with oxygen results in increased or accelerated conversion of biologically active TNF-alpha to its inactive form. Such degradation, prior to, and during, current assay procedures is of concern when using samples containing biologically active TNF-alpha. Another aspect of this invention, therefore, pertains to a method for blocking the degradation of TNF-alpha in a biological (e.g. blood-derived) sample by contacting the sample with an anti-oxidant. The method comprises combining an anti-oxidant with fresh biological sample containing TNF-alpha in an amount sufficient to block accelerated degradation of TNF-alpha biological activity. As used herein, the term "accelerated degradation" refers to any process such as dissociation of the TNF-alpha oligomer, that leads to reduced TNF-alpha biological activity in fresh blood-derived biological samples. As used herein, the expression "anti-oxidant" means a composition which is capable of sequestering oxygen from a blood-derived sample, thus inhibiting the accelerated degradation of TNF-alpha. Suitable biological samples include whole blood, serum, plasma, pleural and serous effusions, and peritoneal ascites. Preferably the anti-oxidant is an organic sequestering agent such as ethylenediamine tetraacetic acid-EDTA (Merck Index, compounds 3486-3489, 10th Edition) luminol, or a combination thereof. EDTA is most preferably employed at a concentration of from about 5 to about 25 mM and luminol is most preferably employed at a concentration of from about 1 to about 4 mM.

The invention is further described in the following examples wherein all parts and percentage are by weight and degrees are Celsius unless otherwise stated.

EXAMPLES

Example 1

TNF-alpha Radio-Immunometric Assay (TNF-RIA)

Human mononuclear cells were isolated from fresh human blood by the Ficoll-Paque method followed by selection of the adherent cell population. The cells were suspended in RPMI1640 tissue culture medium supplemented by 10% fetal calf serum and glutamine. The cells were stimulated to release TNF into the medium by the addition of varying amounts of LPS from *E. coli*. After an incubation of 21 hours at 37° C., aliquots of supernatant were removed from each culture, the cells were removed by centrifugation and 200 uL of each supernatant were assayed in the following TNF RIA.

TNF RIA

Polystyrene beads (0.625 cm diameter) are coated with a monoclonal antibody reactive with an epitopic site on the TNF monomer, designated 104 MAb, at a concentration of 0.5-5.0 ug per bead in a PBS buffer volume of 200 ul per bead for 4-18 hours at ambient temperature. The coated beads are cured with buffer volume of 200 ul per bead, containing 1% BSA and 2-5% sucrose, and preferably dried. In the assay, the beads are contacted with four hundred microliters of a sample suspected of containing TNF and the resulting combination was incubated for two hours at 37° C. Additionally, the same volume of TNF standards, ranging in concentration from 0 to 5,000 pg/ml of recombinant human TNF-alpha previously lyopholized in PBS-BSA-NaCl buffer and reconstituted prior to use, are contacted with the beads under the same incubation conditions.

Following the two hour incubation period, the beads are washed with 15 mls of deionized H₂O to remove excess material. The beads are then incubated for two hours at ambient temperature with 200 ul of TNF RIA tracer, consisting of Mab 104 labeled with $^{125}$I. The antibody was labeled using the chloramine T method and brought up to desired concentration (400,000 dpm—decays per minute per 200 ul) using a buffer.

Following the second two hour incubation, the beads are washed again with 15 mls of deionized H₂O to remove excess tracer. The radioactivity on each bead is then counted in a gamma counter and a standard curve, is constructed by plotting the average cpm (counts per minute) obtained for each TNF standard on the vertical (Y) axis versus corresponding TNF concentration on the horizontal (X) axis. Cpm (count per minute) values for samples are then read from the standard curve to determine the TNF concentration.

was similar in blood and serum indicating that they can be applied when the blood is drawn.

TABLE I

| Reagent |        | Buffer | Percent Recovery (Buffer = 100%) | | | | | Avg ± SD |
|---------|--------|--------|--------|---------|---------|---------|---------|----------|
|         |        |        | Serum1 | Serum2  | Serum3  | Serum4  | Serum5  |          |
| Buffer  |        | 100    | 52     | 54      | 54      | 58      | 61      | 56 ± 4   |
| Luminol | 2 mM   | 89     | 97     | 83      | 98      | 96      | 88      | 92 ± 7   |
| Luminol | 1 mM   | 94     | 87     | 79      | 79      | 90      | 83      | 84 ± 5   |
| EDTA    | 10 mM  | 96     | 89     | 83      | 94      | 92      | 86      | 89 ± 4   |
| EDTA    | 5 mM   | 102    | 93     | 94      | 79      | 90      | 65      | 84 ± 12  |

| Results: | |
|----------|---|
| LPS (mg/ul) | TNF pg/ul |
| 100 | 5,050 |
| 10 | 2,220 |
| 1 | 1,910 |
| 0 | 610 |

The TNF RIA of Example 1 was capable of detecting TNF-alpha of human macrophage origin. The TNF production was dependent on dose of LPS.

Example 2
Method for Preventing Degradation of TNF in Blood

Freshly obtained serum samples from 5 healthy individuals were used to dilute human TNF-alpha of recombinant DNA origin. Prior to exposure of TNF-alpha to the serum, various concentrations of Luminol or EDTA were added to aliquots of serum samples. Buffer (0.1 M Phosphate buffer, 1.85% NaCl, 0.1% NaN₃) was used as a control reagent. 600 pg/mL of TNF-alpha were added to the samples shown in Table 1 and the resulting mixtures were incubated for 10 minutes before assaying for TNF-alpha reactivity by the above TNF-RIA. The results in Table 1 indicate that EDTA or Luminol prevent a significant loss of TNF-alpha reactivity.

EDTA or Luminol was added to whole blood or serum of the same individuals. The effect of the reagents Example 3
TNF RIA/Bioassay Comparison Recombinant human TNF-alpha was calibrated in cytotoxicity assay and then assayed in the above-described TNF RIA. As shown in FIG. 1, there is excellent agreement between known TNF-alpha levels (Centocor TNF standard) and those obtained using a Mab 104-based immunoassay. The agreement between bioassay and the 104-based immunoassay was also found to be close when TNF-alpha was partially heat inactivated. The results in FIG. 2 indicate that TNF RIA is measuring biologically active TNF since both sets of curves track each other.

Equivalents

Those skilled in the art will recognize or be able to ascertain, using no more than routine experimentation, many equivalents of the specific embodiments of the invention described herein. Such equivalents are intended to be encompassed by the following claims.

I claim:

1. An immunometric assay for biologically active TNF-alpha in a biological fluid comprising:
   a. combining the biological fluid with EDTA at a concentration of from 10 mM to 25 mM;
   b. forming a ternary complex of:
      i. a first antibody that is labeled, specific for an epitope of human biologically active TNF-alpha;
      ii. a second antibody specific for the same epitope of human biologically active TNF-alpha; and
      iii. human biologically active TNF-alpha;
   c. detecting the amount of label associated with the complex formed form the components in step b., as indicative of the quantity of biologically active human TNF-alpha in the sample.

2. A method for preventing the loss of bioactivity of human TNF-alpha in a biological sample, comprising combining the TNF-alpha in the sample with EDTA at a concentration of from 10 mM to 25 mM to prevent the accelerated degradation of TNF-alpha.

3. A method for preventing the loss of bioactivity of human TNF-alpha in plasma, comprising combining the TNF-alpha in the plasma with EDTA at a concentration of from 10 mM to 25 mM to prevent the accelerated degradation of TNF-alpha.

4. A method for preventing the loss of bioactivity of human TNF-alpha in a biological sample, consisting of combining a biological sample containing TNF-alpha directly with an amount of luminol sufficient to prevent the accelerated degradation of TNF-alpha.

5. A method of claim 4, wherein the luminol concentration is form about 1 to 4 mM.

6. A method for preventing the loss of bioactivity of human TNF-alpha in a biological sample, comprising combining a biological sample containing TNF-alpha in the sample with an amount of EDTA and luminol sufficient to prevent the accelerated degradation of TNF-alpha.

7. A method of claim 6, wherein the concentration of EDTA is from 10 to 25 mM and the concentration of luminol is from about 1 to 4 mM.

8. An immunometric assay for biologically active TNF-alpha in a biological fluid comprising the following steps in the order shown:
   a. combining the biological fluid with luminol at a concentration of from about 1 to 4 mM;
   b. forming a ternary complex of:
      i. a first antibody that is labeled, specific for an epitope of human biologically active TNF-alpha;
      ii. a second antibody specific for the same epitope of human biologically active TNF-alpha; and
      iii. human biologically active TNF-alpha;
   c. detecting the amount of label associated with the complex formed from the components in step b., as indicative of the quantity of biologically active human TNF-alpha in the sample.

* * * * *